(12) United States Patent
Hoeck et al.

(10) Patent No.: US 6,620,428 B1
(45) Date of Patent: Sep. 16, 2003

(54) TRANSDERMALLY ADMINISTERED ACETYLCYSTEINE AS MUCOLYTIC AGENT

(75) Inventors: Ulla Hoeck, Hillerød (DK); Bo Kreilgard, Hillerød (DK); Christina Nathansen, Hillerød (DK)

(73) Assignee: Pharmacia AB, Stockholm (SE)

(*) Notice: Subject to any disclaimer, the term of this patent is extended or adjusted under 35 U.S.C. 154(b) by 0 days.

(21) Appl. No.: 09/171,673
(22) PCT Filed: Mar. 21, 1997
(86) PCT No.: PCT/SE97/00483
§ 371 (c)(1), (2), (4) Date: Oct. 23, 1998
(87) PCT Pub. No.: WO97/39741
PCT Pub. Date: Oct. 30, 1997

(30) Foreign Application Priority Data

Apr. 23, 1996 (SE) .................................. 9601527

(51) Int. Cl.⁷ ......................... A61K 9/70; A61L 15/16; A61F 13/00; A61N 1/30
(52) U.S. Cl. ................... 424/449; 424/447; 424/448
(58) Field of Search ................ 424/447, 448, 424/449; 604/20

(56) References Cited

FOREIGN PATENT DOCUMENTS

| EP | 0481294 | | 4/1992 |
| WO | 95 00136 | | 1/1995 |
| WO | WO95/00136 | * | 1/1995 |
| WO | 96 00060 | | 1/1996 |

* cited by examiner

Primary Examiner—Shelley A. Dodson
(74) Attorney, Agent, or Firm—Birch, Stewart, Kolasch & Birch, LLP

(57) ABSTRACT

Device for transdermal administration of N-Acetyl-L-cysteine, optionally encompassing salts, prodrugs and metabolites thereof, optionally together with pharmaceutically acceptable carrier(s) to a human being or an animal in order to achieve a mucolytic effect. Use of a mucolytic compound comprising N-Acetyl-L-cysteine, optionally encompassing salts, prodrugs and metabolites thereof, optionally together with pharmaceutically acceptable carrier(s), for the manufacture of a composition for achieving a mucolytic effect in a human being or an animal. Method for achieving a mucolytic effect in a living body by transdermal administration of a compound comprising N-Acetyl-L-cysteine, optionally encompassing salts, prodrugs and metabolites thereof, optionally together with pharmaceutically acceptable carrier(s).

10 Claims, 4 Drawing Sheets

MATRIX

MULTI-LAMINATE

RESERVOIR

DRUG-IN-ADHESIVE

TRANSDERMALLY ADMINISTERED ACETYLCYSTEINE AS MUCOLYTIC AGENT

This application is the national phase under 35 U.S.C. §371 of prior PCT International Application No. PCT/SE97/00483 which has an International filing date of Mar. 21, 1997 which designated the United States of America, the entire contents of which are hereby incorporated by reference.

This invention relates to use of N-Acetyl-L-cysteine, optionally encompassing salts, prodrugs and metabolites thereof, for the manufacturing of a medicament to be administered transdermally for achieving a mucolytic effect and to methods of treating diseases being treatable with a mucolytic agent by transdermal administration of N-Acetyl-L-cysteine, optionally encompassing salts, prodrugs and metabolites thereof.

BACKGROUND

N-Acetyl-L-cysteine, $C_5H_9NO_3S$, is an expectorant. Its synthesis was disclosed in Smith et al., J. Org. Chem., 1961;26:820. N-Acetyl-L-cysteine decreases the viscosity of mucous and purulent expectorate. The mucolytic effect after peroral administration in connection with bronchitis is though not well-documented. However, several investigations have proved effect just below the significance limit. Anyhow, the patients' wellbeing during treatment with N-Acetyl-L-cysteine is significant. N-Acetyl-L-cysteine is registered as a mucolytic agent for peroral administration under trade marks such as Fabrol®, Inspir® and Mucomust®.

N-Acetyl-cysteine has a low bioavailability, only about 4–10%, when administered perorally, see Mack R. Holdiness, "Clinical Pharmacokinetics of N-Acetylcysteine", Clin. Pharmacokinet., 1991;20(2):123–134. The following references confirm the low bioavailability of N-Acetyl-L-cysteine: L. Borgström et al., "Pharmacokinetics of N-Acetylcysteine in Man", Eur J Clin Pharmacol. 1986;31:217–222, L. Borgström et al., "Dose dependent pharmacokinetics of N-Acetylcysteine after oral dosing to man", Biopharmaceutics & Drug Disposition, 1990(II):131–136, B. Olsson et al., "Pharmacokinetics and Bioavailability of Reduced and Oxidized N-Acetylcysteine", Eur J Clin Pharamcol. 1988;34:77–82. Martindale, "The Extra Pharmacopoeia", London, 1993, recommends a peroral dosing of 200 mg three times daily to adults, 200 mg once daily for children up to 2 years and 200 mg twice daily for children aged 2 to 6 years.

Deutsche Apotheker Zeitung; 34; 1990 indicates that the maximum plasma level is reached 2 to 3 hours after oral administration. The same reference indicates 4% bioavailability upon oral administration.

Currently the mucolytic effect is achieved by inhalation or peroral administration of N-Acetyl-L-cysteine. The inhalation route can only be used for temporary relief and several dosings per day are necessary. Administration of N-Acetyl-L-cysteine through the oral route is hampered by a low bioavailability of the drug due to an extensive first-pass metabolism and side effects such as nausea and skin disorders, like rash.

The above disadvantages are removed or reduced upon administering N-Acetyl-L-cysteine transdermally.

N-Acetyl-L-cysteine is a fairly unstable drug in aqueous formulation. This could be improved by incorporation into a lipophilic medium like the one used in pressure sensitive adhesives, such as polyisobutylenes, acrylates and silicone derivatives.

PRIOR ART

Transdermal administration of N-Acetyl-L-cysteine is known from a few patents, e.g. from WO 95/00136 (ARNDT ET AL.) for treating hyperkeratosis, and WO 93/07903 (DECKNER ET AL.) wherein is disclosed certain cationic polymers which may improve transdermal penetration of a number of drugs, such as N-Acetyl-L-cysteine. Anyhow there is no patent which discloses transdermal administration of N-Acetyl-L-cysteine for achieving a mucolytic effect.

EP 0481294 (SPIRIG AG) discloses oral administration of acetylcysteine, but does not mention transdermal administration thereof.

Only sparse studies on skin permeation of N-Acetyl-L-cysteine have been reported in the literature with the aim to use N-Acetyl-L-cysteine as a model substance in connection with experiments to compare skin permeability between different animal species such as rat, rabbit, pig, monkey and man, see Methodius J. Bartek et al., "Skin permeability in vivo in rat, rabbit, pig and man", 32nd Annual Meeting of the Society for Investigative Dermatology Inc., Boston, Mass., 1971, June 18–20, and Ronald C. Wester et al., Clin. Pharmacokinet., 1992;23(4):253–266. From inter alia the above Bartek reference it is evident that the transdermal pene-tration of N-Acetyl-L-cysteine hitherto was considered to be very low.

There is no literature reference which discloses transdermal administration of N-Acetyl-L-cysteine for achieving a mucolytic effect.

Hence the present invention being transdermally administered N-Acetyl-L-cysteine as mucolytic agent, as further described below, is both new and inventive over prior art.

OBJECTS OF THE INVENTION

The above mentioned disadvantages and side effects are removed or reduced when N-Acetyl-L-cysteine is administered transdermally.

Accordingly, a first object of the present invention is to provide a device for transdermal administration of N-Acetyl-L-cysteine, optionally encompassing salts, prodrugs and metabolites thereof, for achieving a mucolytic effect. The administration can be to a human being or to an animal. The mucolytic effect is for treating any kind of mucous and purulent expectorates, such as, but not exclusively, mucous and purulent expectorates occuring in association with upper and lower respiratory infections, including chronic bronchitis and asthma, and with cystic fibrosis, emphysema, tracheostomy and post-operative pulmonary complications. The pharmacological effect is primarily achieved by reduction of the viscosity for the mucous and purulent expectorates.

A second object of the invention is to provide use of a mucolytic compound comprising N-Acetyl-L-cysteine for the manufacture of a composition to be administered transdermally for treating mucous and purulent expectorates, primarily by decreasing their viscosity, or conditions associated with mucous and purulent expectorates.

A third object of the invention is to provide a method of treating diseases, in humans or animals, which are treatable with mucolytic agents by administering N-Acetyl-L-cysteine transdermally.

Other objects of the invention will become apparent to one skilled in the art, and still other objects will become apparent hereinafter.

SUMMARY OF THE INVENTION

The present invention relates to transdermal administration of N-Acetyl-L-cysteine, optionally encompassing salts, prodrugs and metabolites thereof for achieving a mucolytic effect. This effect is primarily achieved through the systemic effect of N-Acetyl-L-cysteine whereby in the first place the viscosity of mucous and purulent expectorates is decreased. Anyhow, other mechanisms of actions are not excluded.

DETAILED DESCRIPTION OF THE INVENTION

Figure 1A:
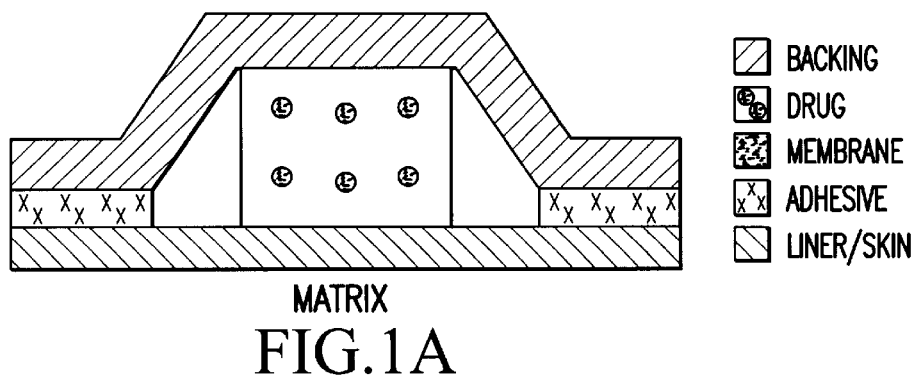
FIGS. 1A–1D are schematic drawings of different types of devices for transdermal delivery of drugs.
Figure 1B:
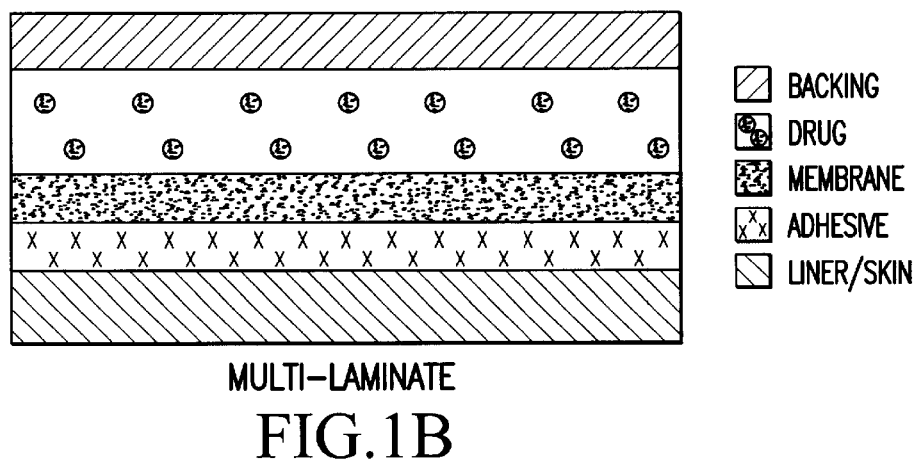
Figure 1C:
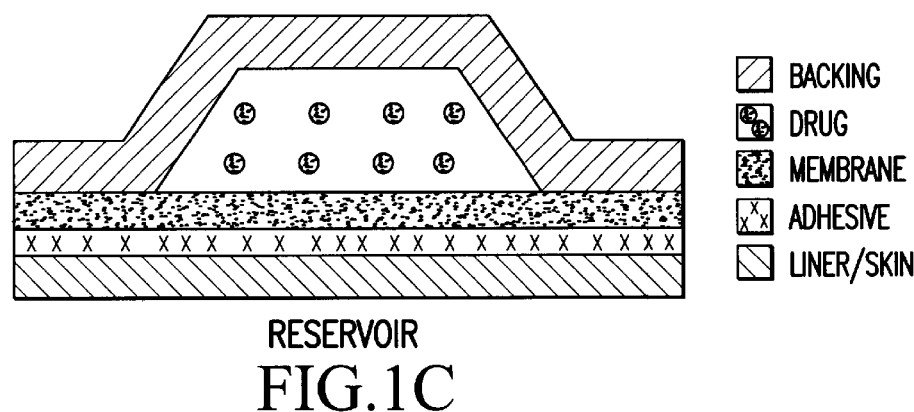
Figure 1D:
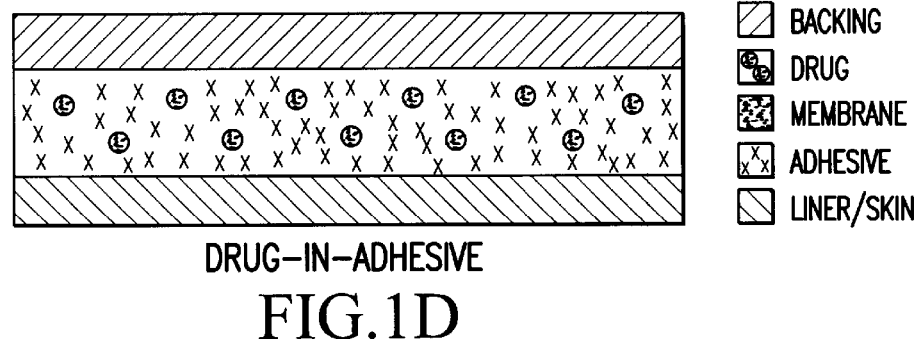

Transdermal delivery of drugs can be accomplished from topical products such as ointments or cremes or from transdermal devices. The present invention relates to administration via transdermal devices, which usually are called transdermal patches.

Devices usable as transdermal patches can be categorized in many different ways. A comprehensive categorization of transdermal devices is found in Steven Wick, "Developing A Drug-In-Adhesive Design For Transdermal Drug Delivery", Adhesives Age, 1995; 38(10):18–24, which hereby is incorporated by reference. Wick essentially divides transdermal devices into the below four main groups:

- the reservoir type, in which the drug is placed in a liquid or a gel and is delivered to the skin across a rate-moderating membrane;
- the matrix type, in which the drug is placed within a non-adhesive polymeric material, typically a hydrogel or soft polymer;
- the drug-in-adhesive type, in which the drug is placed within an adhesive polymer;
- the multi-laminate type, which is similar to the drug-in-adhesive design, but which incorporates an additional layer of pressure sensitive adhesive to cover the entire device and affix it to the skin.

The above four main types of transdermal devices are schematically illustrated in FIGS. 1A–1D.

A fifth important type, not mentioned by Wick, is the iontophoretic type, in which an electrical potential gradient is used for transferring the drug through the skin—see further e.g. Parminder Singh et al, "Iontophoresis in Drug Delivery: Basic Principles and Applications", Critical Reviews in Therapeutic Drug Carrier Systems, 1994; 11 (2&3):161–213.

The above split-up into groups is not very strict as variations and combinations of each may be envisaged. So may a multi-laminate type device encompass a device with many layers in a sandwich construction, such as the drug in one layer, excipients such as enhancers in a further layer, a membrane in another layer and an adhesive in still another layer. Or it could be composed of several drug-in-adhesive layers or combinations of the above layers.

The liquid or gel used in the above reservoir type device could be hydrophilic or lipophilic, such as water, alcohols, mineral oils, silicone fluids, various copolymers, such as ethylene vinyl acetate, vinyl acetate or polyvinyl alcohol/polyvinyl pyrrolidine. The reservoir may also include dyes, inert fillers, diluents, antioxidants, penetration enhancers, stabilizers, solubilizing agents and other pharmacologically inactive pharmaceutical agents being well known in the art.

The adhesives used are generally of three types, being the rubber type, encompassing inter alia polyisobutylenes, the acrylate type and the silicone type. The adhesives may be chemically modified and may have a wide range of molecular weights. To the adhesive could be added several types of excipients such as fillers, stabilizers, plasticizers, buffering agents, penetration enhancers, penetration retarders, solubilizing agents and other pharmaceutical ingredients being well known in the art.

Polymer films which may be used for making the rate-moderating membrane include, without limitation, those comprising low density polyethylene, high density polyethylene, ethyl vinyl acetate copolymers and other suitable polymers.

The backing layer serves the purposes of preventing passage of the drug or environmental moisture through the surface of the patch distant from the skin, and also for providing support for the system, where needed. The backing layer may be choosen so that the end product is appealing to the users, whether children, adults, elderly people or other customer groups. The backing layer is impermeable to the passage of N-Acetyl-L-cysteine or inactive ingredients being present in the formulation and can be flexible or nonflexible. Suitable materials include, without limitation, polyester, polyethylene terephthalate, some types of nylon, polypropylene, metallized polyester films, polyvinylidene chloride and aluminium foil.

The release liner can be made of the same materials as the backing layer.

As will be clear further below the invention according to the present application encompasses administration of N-Acetyl-L-cysteine via all hitherto known types of devices for transdermal administration. Mainly the above categorization will be adhered to in this application. Anyhow, this does not exclude that transdermal devices which might fit better according to some other categorization also are included in the present invention.

It is well known in the art that the properties of the skin as such influence the penetration of the drug through the skin into the systemic circulation. It could thus be said that the skin controls the drug penetration rate. Anyhow, as the skin as such is no part of the present invention the behaviour of the skin in connection with transdermal administration will not be discussed in detail. It is also well accepted in the art that when rate controlling properties are attributed to a transdermal device is meant properties associated with the release rate from the device as such. It is also evident that when a transdermal device is designed to exhibit a certain release performance the properties of the skin need be taken into consideration during the design process.

The rate control ability is often a very important feature for a transdermal device in order to deliver the correct drug amount to the patient at the correct time. Thereby maximum efficacy is achieved while side effects are minimized. Many factors influence the rate control ability of a transdermal device. In the below Table 1 the most important such factors are listed and their influence in the respective device type is marked. A plus sign indicates that the influence is strong. The absence of a plus sign does not exclude that the corresponding factor has at least some influence.

TABLE 1

TYPE OF DEVICE

| Factor | Reservoir | Matrix | Drug-in-adhesive | Multi-laminate |
|---|---|---|---|---|
| -Polymer type(s) | + | + | + | + |
| -Modification of the polymer(s) | | + | + | + |
| -Activity, i.e. concentration, of drug, e.g. supersaturation | + | + | + | + |
| -Additives in polymer(s) | | | | |
| Enhancer(s) | + | + | + | + |
| Cyclo-dextrine(s) | + | + | + | + |
| Retarder(s) | + | + | + | + |
| -pH-adjustment | + | + | + | + |
| -Solubilizer(s) | + | + | + | + |
| -Emulsifier(s) | + | + | + | + |
| -Membrane(s) | + | | | |
| Hydrophilic | + | | | |
| Lipophilic | + | | | |
| Thickness | + | | | |
| Pore Size | + | | | |
| Density | + | | | |
| -Chemical stabilizer(s) | + | + | + | + |

As a comparably high loading of N-Acetyl-L-cysteine is needed for achieving the desirable therapeutic effect the reservoir type device and the multilaminate type device, including several drug-containing layers, are presently considered to be the best modes for making the present transdermal delivery of N-Acetyl-L-cysteine.

It is also desirable to include, at least in some device types, one or more transdermal penetration enhancing substance(s) in order to increase the amount of N-Acetyl-L-cysteine that may penetrate the skin and that eventually may reach the systemic cirkulation. Enhancers suitable in the present invention may be categorized in the below groups, although enhancers not belonging to any of these groups are not excluded.

- alcohols, such as short chain alcohols, e.g ethanol and the like, long chain fatty alcohols, e.g. lauryl alcohols, and the like, and polyalcohols, e.g. propylene glycol, glycerin and the like;
- amides, such as amides with long aliphatic chains, or aromatic amides like N,N-diethyl-m-toluamide;
- amino acids;
- azone and azone-like compounds;
- essential oils, i.e. essential oils or constituents thereof, such as 1-carvone, 1-menthone and the like;
- fatty acids and fatty acid esters, such as oleic acid, lauric acid and the like, further esters of fatty acids, such as isopropyl myristate, and various esters of lauric acid and of oleic acid and the like;
- macrocyclic compounds, such as cyclopentadecanone and cyclodextrins;
- phospholipid and phosphate compounds, such as phospholipids;
- 2-pyrrolidone compounds; and
- miscellaneous compounds, like sulphoxides, such as dimethyl sulphoxides, and fatty acid ethers, such as Laureth-9 and polyoxylaurylether.

Combinations of enhancers from different groups in the above cathegorization may prove to be very useful and efficient.

For overviews of enhancers, see further e.g. G.C. Santus et al., "Transdermal enhancer patent literature", Journal of Controlled Release, 1993;25:1–20 and Eric W. Smith et al., "percutaneous penetration enhancers",CRC Press Inc., 1995.

DETAILED DESCRIPTION OF THE INVENTION

The following examples are intended to illustrate but not to limit the scope of the invention, although the embodiments named are of particular interest for our intended purposes.

MATERIALS AND APPARATUS USED IN THE EXAMPLES

Materials

N-Acetyl-L-cysteine, Fluka

Sodium hydroxide, Merck

Propylene glycol, Merck

Azone, Discovery Therapeutics Inc.

Ethanol 99.9%, De Danske Spritfabrikker

Hydrochloric acid, Merck

Polycarbonate membrane 0.2 $\mu$m in pore diameter, Whatman

Polycarbonate membrane 0.6 $\mu$m in pore diameter, Whatman

Polyester membrane 0.2 $\mu$m in pore diameter, Whatman

Polyester membrane 0.6 $\mu$m in pore diameter, Whatman

Cotran 9711, 3M

Polyester film S 2016, Rexam Release

Polyester film Scotchpak 1220, 3M

Polyester film Scotchpak 1109, 3M

Eudragit RL 30 D, Röhm GmbH Chemische Fabrik

Eudragit NE 30 D, Röhm GmbH Chemische Fabrik

Plastoid E35H, Röhm GmbH Chemische Fabrik

Polyvidone 90, BASF

Span 20, Sorbitanmonolaurate, Maximex

MA-24 Medical Grade Adhesive, Adhesives Research Inc.

ETA-2 Medical Grade Adhesive, Adhesives Research Inc.

Durotak 387–2287, National Starch and Chemical B.V.

Triethyl citrate, Fluka

Sodium bisulfite, Sigma

Apparatus

Franz diffusion cells

Coating equipment: RP Print Coat Instrument LTD., Type KCC 202 Control Coater System with vacuum bed and rods (100 and 400 $\mu$m)

UV-spectrophotometer

Drug Release Apparatus 5, paddle over disk,.described in USP 23, p. 1797

HPLC-device: LKB 2150 pump

LKB 2141 variable wavelength monitor

LKB 2221 integrator

Marathon-XT autosampler (20 $\mu l$ injected) connected to a Multi Temperature 111 cooling bath adjusted to 4° C.

Analytical column, 25 cm×4.0 mm i.d., packed with Lichrosorb RP18, 5 $\mu$m.

The column was eluted isocratically at ambient temperature with a mobile phase consisting of water-acetonitrile (970:50 v/v) adjusted with diluted phosphoric acid to a pH=3. The flow rate was 1.0 ml/min. and the column effluent was monitored at 220 nm.

Example 1

Analysis of the receptor solutions described in Examples 2 and 3, and of the stability samples described in Example 6.

Quantitative determination of N-Acetyl-L-cysteine in the receptor solution samples from the skin permeation studies in Example 2 and from the membrane permeation studies in Example 3, and quantitative determination of N-Acetyl-L-cysteine in the samples from the stability studies in Example 6, was done by the HPLC method described under Apparatus.

Example 2

In vitro skin permeation studies from solutions of N-Acetyl-L-cysteine.

Solution 1

500 mg N-Acetyl-L-cysteine was dissolved in 5 ml demineralized water.

The pH of the solution was adjusted to 5 by the addition of sodium hydroxide.

Solution 2

250 mg N-Acetyl-L-cysteine was dissolved in 5 ml propylene glycol.

Solution 3

250 mg N-Acetyl-L-cysteine was dissolved in 5 ml propylene glycol containing 50 mg/ml of azone.

Solution 4

500 mg N-Acetyl-L-cysteine was dissolved in 5 ml ethanol.

In vitro permeation of N-Acetyl-L-cysteine from the solutions 1, 2, 3 and 4 through dermatomed pig skin was investigated in Franz diffusion Cells.

Skin pieces with a thickness of approximately 765 $\mu$m were dermatomed from full thickness pig skin and mounted in glass diffusion cells with an available diffusion area of 1.8 cm$^2$. Pig skin is a fully accepted model for human skin. The solutions 1, 2, 3 and 4 were applied separately on the skin surfaces and the dermal sides were all exposed to 12.1 ml receptor solution consisting of 0.0001M hydrochloric acid equilibrated to 37±1° C.

Figure 2:
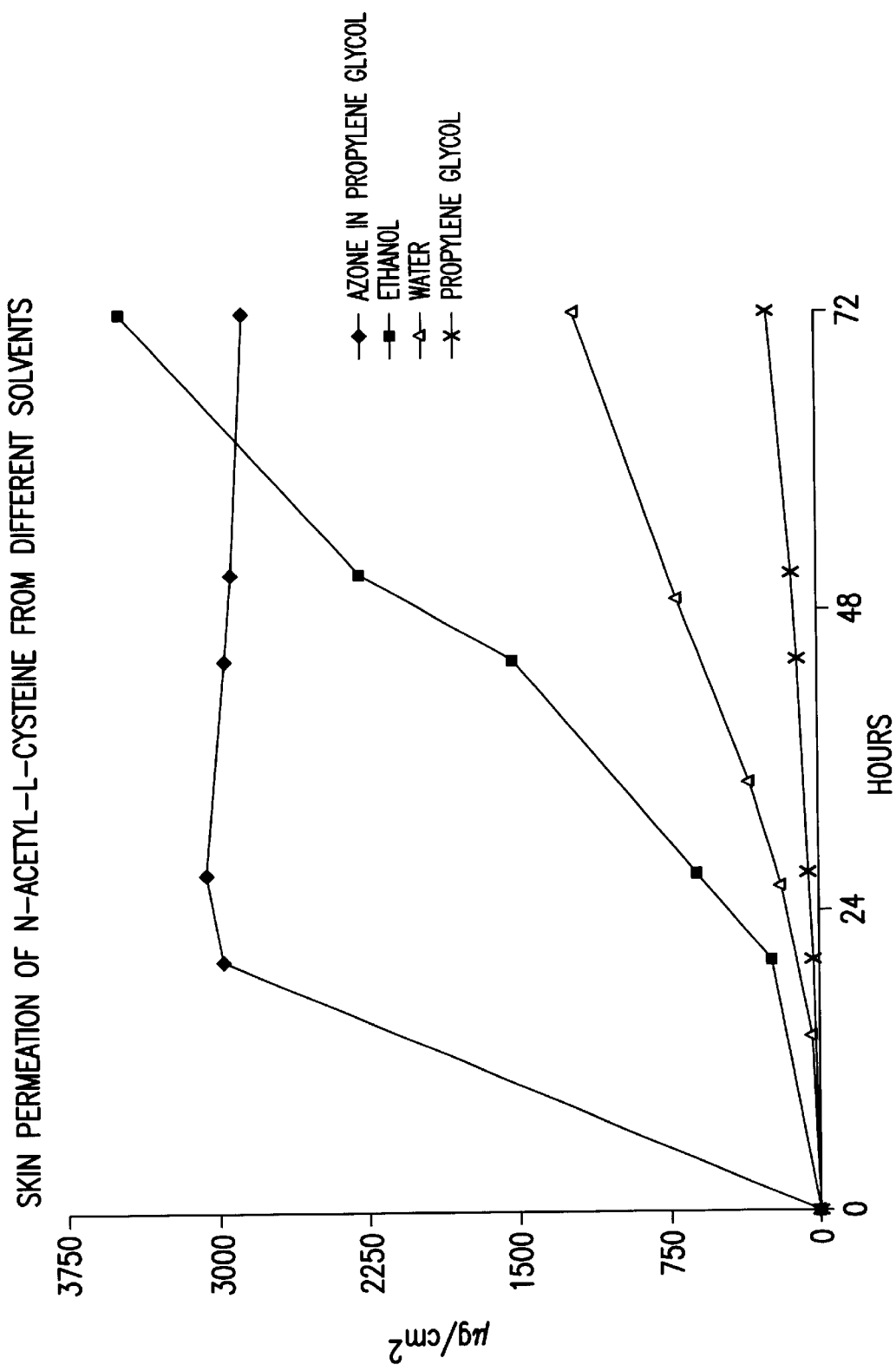
FIG. 2 is a diagram showing in vitro skin permeation of N-Acetyl-L-cysteine from different solvents according to Example 2.

Permeation of N-Acetyl-L-cysteine was followed by removing samples periodically and measuring the concentration by the HPLC method according to Example 1. The cumulative amount of N-Acetyl-L-cysteine appearing in the receptor solution versus time is shown in FIG. 2. An increase in the permeated amount of N-Acetyl-L-cysteine is seen in the following order: Propylene glycol, water, ethanol and propylene glycol containing 5% azone added used as solvents. The estimated fluxes of N-Acetyl-L-cysteine are in the range from approximately 4 to 48 $\mu$g/cm$^2$/h for the above solvents without enhancer added. The results show that it is possible to optimize the flux of N-Acetyl-L-cysteine through the skin by using an appropriate solvent. A surprisingly high rate of permeation was observed for the solution with added azone as about 3000 $\mu$g/cm$^2$ was permeated after 20 hours.

Example 3

In vitro permeation studies across artificial membranes from solutions of N-Acetyl-L-cysteine, imitating the reservoir type transdermal device.

Solution 5

50 mg N-Acetyl-L-cysteine was dissolved in 5 ml demineralized water.

Solution 6

50 mg N-Acetyl-L-cysteine was dissolved in 5 ml ethanol.

In vitro permeation of N-Acetyl-L-cysteine from the solutions 5 and 6 across 5 different types of artificial membranes was investigated in Franz diffusion cells.

Figure 3:
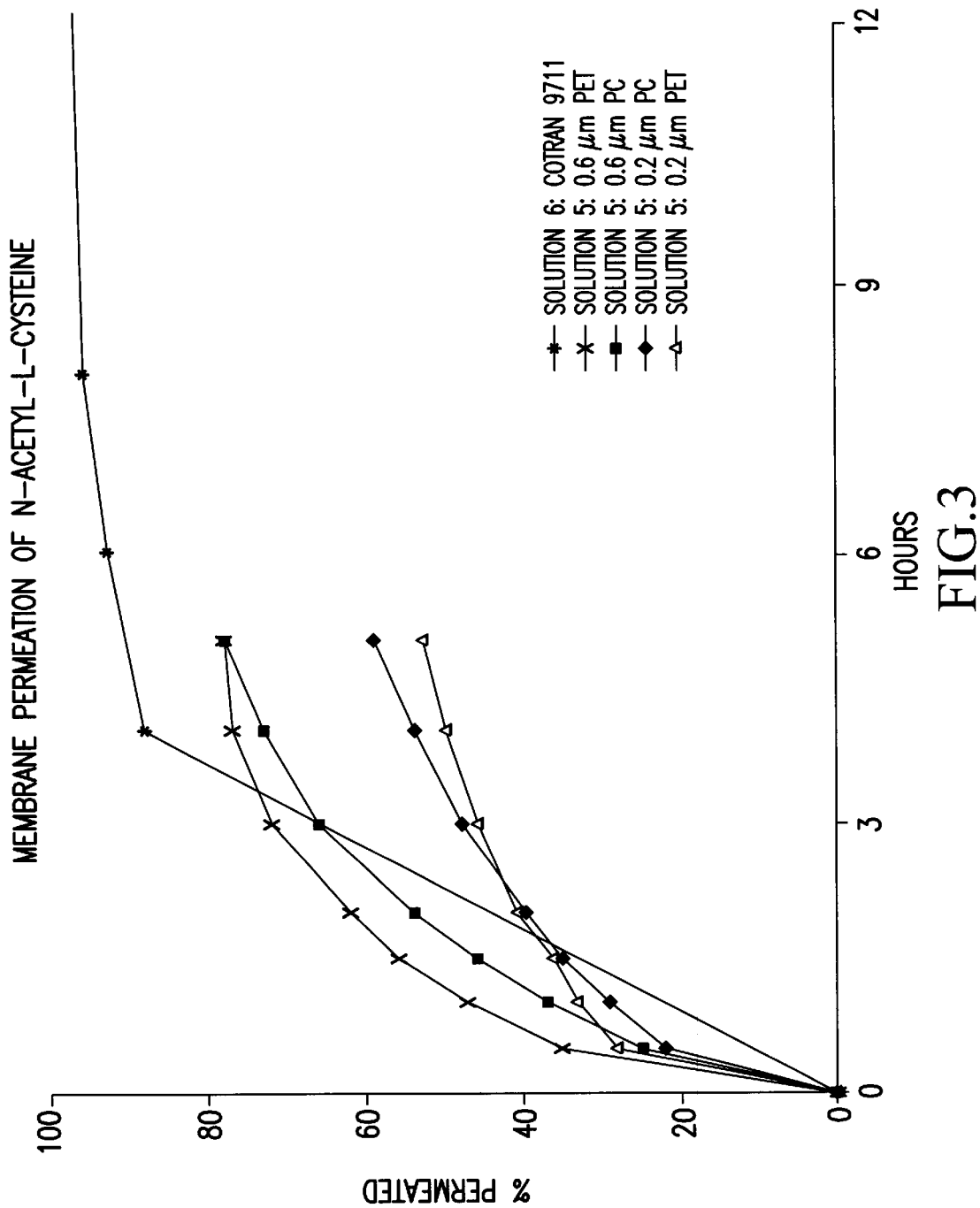
FIG. 3 is a diagram showing in vitro permeation of N-Acetyl-L-cysteine through different membranes in accordance with Example 3.

Artificial membranes of the following types were studied: Whatman 0.2 $\mu$m PC (polycarbonate), Whatman 0.6 $\mu$m PC (polycarbonate), Whatman 0.2 $\mu$m PET (polyester), Whatman 0.6 $\mu$m PET (polyester) and Cotran 9711 (microporous polyethylene film). The membranes were mounted in glass diffusion cells with an available diffusion area of 1.8 cm$^2$. Solution 5 was applied on the surfaces on all the above Whatman membranes while solution 6 only was applied on Cotran 9711. The opposite sides of the membranes were all exposed to 12.1 ml receptor solution consisting of 0,0001M hydrochloric acid equilibrated to 37±1° C. Permeation of N-Acetyl-L-cysteine was followed by removing samples periodically and measuring the concentration by the HPLC method according to Example 1. The cumulative amount of N-Acetyl-L-cysteine appearing in the receptor solution versus time is shown in FIG. 3. An increase in the permeated amount of N-Acetyl-L-cysteine is seen in the following order of used membranes: Whatman 0.2 $\mu$m PET, Whatman 0.2 $\mu$m PC, Whatman 0.6 $\mu$m PC, Whatman 0.6 $\mu$m PET and Cotran 9711.

The results show that it is possible to control the release rate of N-Acetyl-L-cysteine from a reservoir type device by the choice of solvent and of membrane.

Example 4

Transdermal drug delivery systems with N-Acetyl-L-cysteine as the active substance.

System 1 (Drug-in-adhesive Type, Acrylate)

2.5 g N-Acetyl-L-cysteine and 350 mg Span 20 were dispersed in 10 g ETA-2 Medical Grade Adhesive to give the drug gel. The drug gel was solvent cast onto a polyester film, S 2016, by means of the coating equipment (wet layer=400 $\mu$m). After drying at 80° C. for 10 minutes, a polyester film, Scotchpak 1220, was laminated onto the dried drug gel. The resulting sheet was die-cut into patches which were kept at room temperature until use. The concentration of N-Acetyl-L-cysteine in the patches was approximately 4 mg/cm$^2$.

System 2 (Drug-in-adhesive Type, Acrylate)

2.5 g N-Acetyl-L-cysteine and 350 mg Span 20 were dispersed in 10 g Durotak 387–2287 to give the drug gel. The drug gel was solvent cast onto a polyester film, S 2016, by means of the coating equipment (wet layer=400 $\mu$m). After drying at 80° C. for 10 minutes, a polyester film, Scotchpak 1220, was laminated onto the dried drug gel. The

System 3 (Drug-in-adhesive Type, Polyisobutylene)

5 g N-Acetyl-L-cysteine and 700 mg Span 20 were dispersed in 20 g MA-24 Medical Grade Adhesive to give the drug gel. The drug gel was solvent cast onto a polyester film, S 2016, by means of the coating equipment (wet layer=400 µm). After drying at 80° C. for 10 minutes, a polyester film, Scotchpak 1220, was laminated onto the dried drug gel. The resulting sheet was die-cut into patches which were kept at room temperature until use. The concentration of N-Acetyl-L-cysteine in the patches was approximately 3 mg/cm$^2$.

System 4 (Multi-laminate Type, Waterbased Acrylate)

4 g N-Acetyl-L-cysteine was dispersed in a mixture of 12.8 g Eudragit RL 30 D, 12.8 g PVP gel (20% Polyvidone 90 swelled in water) and 4 g propylene glycol to give the drug gel. The drug gel was solvent cast onto a polyester film, S 2016, by means of the coating equipment (wet layer=400 µm). After drying at 80° C. for 10 minutes, an adhesive layer con-sisting of Plastoid E35H (wet layer=100 µm) coated on a polyester film, S 2016, was laminated onto the dried drug gel. The polyester film, S 2016, in contact with the drug gel was removed, and Scotchpak 1220 was laminated onto the drug gel as backing. The resulting sheet was die-cut into patches which were kept at room temperature until use. The concentration of N-Acetyl-L-cysteine in the patches was approximately 1,5 mg/cm$^2$.

System 5 (Multi-laminate Type, Waterbased Acrylate)

4 g N-Acetyl-L-cysteine was dispersed in a mixture of 12.8 g Eudragit RL 30 D, 12.8 g PVP gel (20% Polyvidone 90 swelled in water), 4 g propylene glycol and 200 mg 1M sodium hydroxide solution to give the drug gel. The drug gel was solvent cast onto a polyester film, S 2016, by means of the coating equipment (wet layer=400 µm). After drying at 25° C. for 2 hours, an adhesive layer consisting of Plastoid E35H (wet layer=100 µm) coated on a polyester film, S 2016, was laminated onto the dried drug gel. The polyester film, S 2016, in contact with the drug gel was removed, and Scotchpak 1109 was laminated onto the drug gel as backing. The result-ing sheet was die-cut into patches which were kept at room temperature until use. The concentration of N-Acetyl-L-cysteine in the patches was approximately 1,5 mg/cm$^2$.

System 6 (Multi-laminate Type, Waterbased Acrylate)

2.4 g N-Acetyl-L-cysteine was dispersed in a mixture of 3 g Eudragit NE 30 D and 45 g Plastoid E35H to give the drug gel. The drug gel was solvent cast onto a polyester film, S 2016, by means of the coating equipment (wet layer=400 µm). After drying at 80° C. for 10 minutes, an adhesive layer consisting of Plastoid E35H (wet layer=100 µm) coated on a polyester film, S 2016, was laminated onto the dried drug gel. The polyester film, S 2016, in contact with the drug gel was removed and Scotchpak 1109 was laminated onto the drug gel as backing. The resulting sheet was die-cut into patches which were kept at room temperature until use. The concentration of N-Acetyl-L-cysteine in the patches was approximately 1 mg/cm$^2$.

System 7 (Drug-in-adhesive Type, Waterbased Acrylate)

2.4 g N-Acetyl-L-cysteine was dispersed in a mixture of 3 g Eudragit NE 30 D and 45 g Plastoid E35H to give the drug gel. The drug gel was solvent cast onto a polyester film, S 2016, by means of the coating equipment (wet layer=400 µm). After drying at 80° C. for 10 minutes, a polyester film, Scotchpak 1109, was laminated onto the dried drug gel. The resulting sheet was die-cut into patches which were kept at room temperature until use. The concentration of N-Acetyl-L-cysteine in the patches was approximately 1 mg/cm$^2$.

System 8 (Multi-laminate Type, Waterbased Acrylate)

4 g N-Acetyl-L-cysteine was dispersed in a mixture of 25 g Eudragit RL 30 D, 1.9 g triethyl citrate, 200 mg 1M sodium hydroxide solution and 20 mg sodium bisulfite to give the drug gel. The drug gel was solvent cast onto a polyester film, S2016, by means of the coating equipment (wet layer=400 mm). After drying at 25° C. for 2 hours an adhesive layer consisting of Plastoid E35H (wet layer=100 mm) coated on a polyester film, S2016, was laminated onto the dried drug gel. The polyester film, S2016, in contact with the drug gel was removed, and Scotchpak 1109 was laminated onto the drug gel as backing. The resulting sheet was die-cut into patches which were kept at room temperature until use. The concentration of N-Acetyl-L-cysteine in the patches was approximately 1 mg/cm$^2$.

Figure 4:
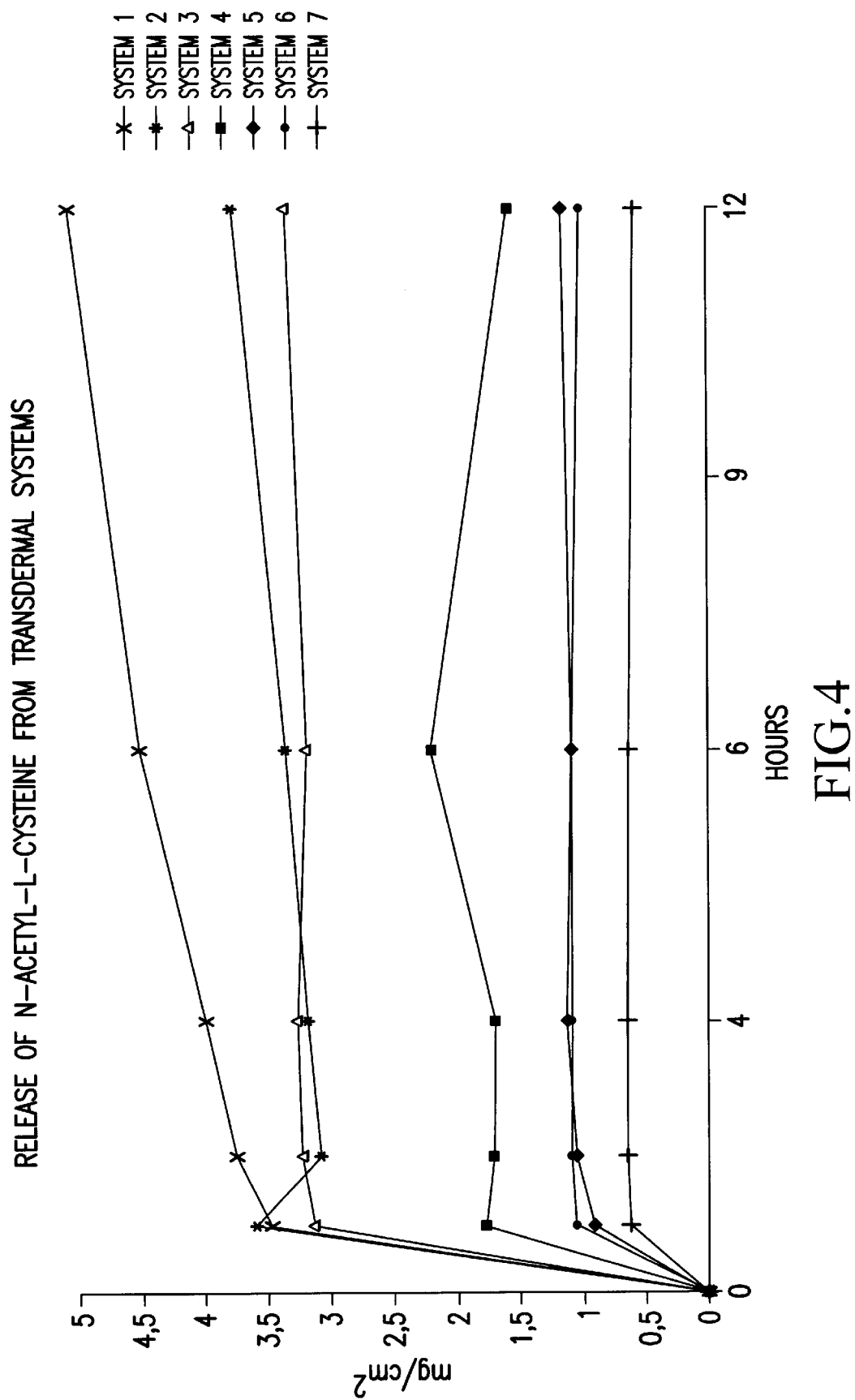
FIG. 4 is a diagram showing in vitro release of N-Acetyl-L-cysteine from different transdermal systems in accordance with Examples 4 and 5.

In vitro release studies according to Example 5 were carried out on the systems 1, 2, 3, 4, 5, 6 and 7 described above. The results of these studies are shown graphically in FIG. 4.

The results show that different release profiles can be achieved from different types of devices.

Example 5

In vitro release studies of the transdermal drug delivery systems 1, 2, 3, 4, 5, 6 and 7 according to Example 4.

The apparatus used was Apparatus 5, paddle over disk, described under Apparatus above. Patches of 7.1 cm$^2$ were applied to the disk assembly, using a suitable adhesive, with the release surface facing up. The dissolution medium used was 600 ml of 0.0001M hydrochloric acid equilibrated to 32±0.5° C. Samples were withdrawn at 1, 2, 4, 8 and 16 hours, respectively. The amount of N-Acetyl-L-cysteine in the samples was determined either by UV-spectrophotometry at 215 nm (Systems 1, 2 and 3) or by the HPLC method described under Apparatus (Systems 4, 5, 6 and 7) and the concentration of the respective systems was expressed in mg N-Acetyl-L-cysteine per cm$^2$.

Example 6

Stability studies were carried out on drug delivery Systems 5 and 8 according to the above Example 4. Patches from these Systems 5 and 8 were stored at room temperature and quantitative determination of N-Acetyl-L-cysteine was done by the HPLC method described under Apparatus after 0, 4 and 12 weeks of storage respectively. The results of these studies are shown in Table 2 below.

TABLE 2

STABILITY OF N-ACETYL-L-CYSTEINE IN PATCHES

| Storage time | Concentration of N-Acetyl-L-cysteine (%) | |
| --- | --- | --- |
| (weeks) | System 5 | System 8 |
| 0 | 100 | 100 |
| 4 | 81 | 97 |
| 12 | 54 | 90 |

The above results show that it is possible to improve the stability of N-Acetyl-L-cysteine in a patch formulation, e.g. by adding a stabilizer such as sodium bisulfite.

A reservoir type device may be manufactured by heat sealing a membrane such as described in Example 3 to a backing containing the drug in a suitable vehicle.

An iontophoretic type device may be manufactured essentially according to embodiments disclosed in e.g. Parminder Singh et al, "Iontophoresis in Drug Delivery: Basic Principles and Applications", Critical Reviews in Therapeutic Drug Carrier Systems, 1994; 11 (2&3):161–213. The administration of N-Acetyl-L-cysteine is not disclosed in this reference. Anyhow it lies within the present invention to modify, using the disclosure in the present application, the embodiments according to said reference to become suitable for the administration of N-Acetyl-L-cysteine.

The above examples show that it is possible to administer N-Acetyl-L-cysteine and to control its release rate using all known types of devices for transdermal drug administration.

Transdermal administration of N-Acetyl-L-cysteine can be improved by use of the prodrug concept. N-Acetyl-L-cysteine is by nature hydrophilic and it is known that hydrophilic drugs may permeate the skin to a limited extent due to an unfavourable partition coefficient between lipids and water. The hydrophilicity of N-Acetyl-L-cysteine could be reduced by chemical modification of the carboxylic group and/or the thiol group. Several pro-drugs of N-Acetyl-L-cysteine are described in Anne H. Kahns et al., "Prodrugs as drug delivery systems. 107. Synthesis and chemical and enzymatic hydrolysis kinetics of various mono- and diesterprodrugs of N-Acetyl-cysteine" are disclosed in Internat. J. Pharma, 1990;62:193–205, but only with the aim of reducing the metabolism of N-Acetyl-L-cysteine in the liver or in the intestine; the authors do not discuss the utility of such pro-drugs for transdermal administration. Pro-drugs of N-Acetyl-L-cysteine may also possess improved characteristics in patch formulations with respect to degradation of N-Acetyl-L-cysteine or to decreased possible skin metabolism.

It is evident that the above mentioned Examples may be modified to encompass also metabolites and prodrugs of N-Acetyl-L-cysteine.

The stability of N-Acetyl-L-cysteine can be improved by the addition of stabilizers, which may prevent degradation of N-Acetyl-L-cysteine. The stabilizers could be disodium edetate, ascorbic acid, sodium bisulphite, sodium hypophosphite, L-cystin, L-cysteine or other suitable stabilizing compounds. Adjustment of the protolytic balance, i.e. pH in aqueous systems, may also increase the stability of patch formulations.

A neglectable degradation of N-Acetyl-L-cysteine, less than 1%, may produce compounds with an unpleasant smell. This smell could be masked by the addition of fragrances or flavouring agents, such as peppermint oil, menthol etc.

As the period of time from the first application of a transdermal device according to the present invention until a therapeutically effective serum level of N-Acetyl-L-cysteine is achieved is in the order 2–3 hours the complementary and concomitant use of another administration form may be of value. Oral, sublingual, buccal, nasal, pulmonary and rectal, or possibly other transmucosal, administration of N-Acetyl-L-cysteine results in that the drug reaches the system more rapidly than through the transdermal route. As mentioned above said non-transdermal administration forms have the disadvantage of a lower bioavailability than the transdermal form of administration. Anyhow this disadvantage, and problems related thereto, may be temporarily tolerated if a mucolytic effect is desirable in the period of time before the therapeutic effect is achieved from the transdermal device.

One suitable use of the mentioned forms of administration is to administer N-Acetyl-L-cysteine through the oral, sublingual, buccal, nasal, pulmonary and rectal, or possibly other transmucosal, route at approximately the same time as the first transdermal device is applied. Thereafter new transdermal devices are applied to ensure the correct plasma level without further administration through the oral, sublingual, buccal, nasal, pulmonary and rectal, or possibly other transmucosal, routes. The above concomitant use of different administration forms is especially useful in certain situations, such as, but not exclusively, some time prior to oral presentations, attendance to conferences and visits to theatres, concerts and church. It is thus feasable to market set of formulations including devices for transdermal administration as well as devices or formulations for oral, sublingual, buccal, nasal, rectal, pulmonary and rectal, and possibly other transmucosal, administration of N-Acetyl-L-cysteine.

Another envisageable concomitant use according to the present invention is to apply a second transdermal device while a priorly applied first trandermal device is still adhered to the patient's skin while still delivering some amount of the drug. The utility behind this use is as follows. Suppose that the transdermal devices used deliver the drug during 36 hours. The first evening one such device is applied. The following evening the device still delivers the drug, though usually with a lower flux rate than earlier. If now this second evening a second transdermal device is applied while the first one is left on the skin the fluxes from the first and second device will add to a useful flux as the flux from the first device successively decreases while the drug from the second device only reaches the systemic circulation after some hours. By using transdermal devices in this way a more stable therapeutically effective plasma level of the drug during an extended period of time is achieved than if for example are used devices delivering for 24 hours and being replaced every 24 hours of course also other useful combinations of concomitantly used transdermal devices are envisageable.

As it might be advantageous that the mucolytic effect during certain periods should be allowed to be minor it might be desirable not to treat mucous and purulent expectorates during too long continuous periods of time. It is within the present invention to administer N-Acetyl-L-cysteine in such a way that a therapeutically effective systemic level of N-Acetyl-L-cysteine prevails mainly during those periods of time during day and night when a mucolytic effect is more desirable, and, consequently, in such a way that a less than therapeutically effective systemic level of N-Acetyl-L-cysteine prevails mainly during those periods of time during day and night when a mucolytic effect is less desirable. The above object is achievable by applying the transdermal device at the appropriate time during day or night in combination with designing the device with the appropriate release profile.

Dosage

Assuming that the oral bioavailability is around 5%, that the transdermal bioavailability is around 100% and that the usual peroral dose is 200–600 mg/day then the transdermal dose is equivalent to 10–30 mg/day. This daily transdermal dose corresponds to a flux rate of 15–45 $\mu g/cm^2$/hour from a transdermal device with an area of 30 $cm^2$ under the assumption that no metabolism takes place in the skin and that the device delivers the drug during 24 hours.

The area of a transdermal device being convenient for a patient to wear is in the range from 5 to 50 $cm^2$. The corresponding patch loading should be at least from about 0.3 $mg/cm^2$ to about 1.0 $mg/cm^2$ for a transdermal device with an area of 30 $cm^2$. As the drug content of a transdermal device is never completely depleted during its application to a patient a higher loading than above must be anticipated, preferably from about 0.5 $mg/cm^2$ to about 3.0 $mg/cm^2$. The above indicated loadings in $mg/cm^2$ are to be considered as average loadings for an average size device. It is known that the driving force for the release of a drug from a transdermal device is related to the drug concentration, i.e. number of mg of drug/$cm^3$. Therefore the above indicated loadings in $mg/cm^2$ are to be adjusted according to the actual areal size and thickness of the device in order to arrive at the desirable therapeutic effect.

Loadings for different sizes and types of devices for transdermal administration, taking into account different age groups and types of patients, range from about 0.1 $mg/cm^2$ to about 10 $mg/cm^2$ of N-Acetyl-L-cysteine. The hourly flux rate of dextromethorphan ranges from about 1 $\mu g/cm^2$/hour to about 100 $\mu g/cm^2$/hour. The effective transdermally delivered amount of N-Acetyl-L-cysteine is from about 0.05 mg/kg bodyweight to about 5 mg/kg bodyweight.

It should also be contemplated that a device for transdermal delivery during 8–12 hours would be clinically more relevant than a device for delivery during 24 hours. Such a device with limited release duration may be used for periods when the problems arising from mucous and purulent expectorates are most embarassing.

The mentioned device may either be taken off from the skin after 8–12 hours in order to stop further delivery, or be designed in such a way that its delivery drops to negligible or non-pharmacological levels after 8–12 hours. In this latter case the device may remain on the skin after 8–12 hours without the patient risking further delivery thereafter which facilitates the patient's handling of the device. Such devices are known per se, see eg U.S. Pat. No. 4,915,950 (MIRANDA ET AL.)—although not for delivery of N-Acetyl-L-cysteine.

When N-Acetyl-L-cysteine is administered in a transdermal device the latter should preferably be occlusive, which means that the device does not permit water to migrate outwardly from the patient. Thereby the hydration of the skin is increased which favors the penetration of N-Acetyl-L-cysteine through the skin.

What is claimed is:

1. A method for achieving a mucolytic effect in a living body by decreasing the viscosity of mucous and purulent expectorates, said method comprising transdermally administering a compound comprising N-Acetyl-L-cysteine, optionally encompassing salts, prodrugs and metabolites thereof, and optionally together with pharmaceutically acceptable carrier(s), wherein transdermal administration is achieved by a transdermal device comprising one or more layers selected from the group consisting of a membrane or an adhesive polymer.

2. The method of claim 1, wherein the mucolytic effect is achieved through systemic effect of the transdermally administered compound.

3. The method of claim 1, or 2, wherein the mucolytic effect is achieved through decreasing the viscosity of mucous and purulent expectorates.

4. The method of claim 1, wherein the transdermal administration is carried out using a device for transdermal delivery, such device is selected from the group consisting of reservoir, matrix, drug-in-adhesive, multi-laminate, iontophoretic and combinations thereof.

5. The method of claim 1, wherein more than one device for transdermal delivery is used at a time.

6. The method of claim 1, wherein the effective amount of N-Acetyl-L-cysteine is from about 0.05 mg/kg bodyweight to about 5 mg/kg bodyweight during a predefined period of time.

7. A method for achieving a mucolytic effect in a living body by decreasing the viscosity of mucous and purulent expectorates, which comprises transdermally administering a compound comprising N-Acetyl-L-cysteine, optionally encompassing salts, prodrugs and metabolites thereof, and optionally together with pharmaceutically acceptable carrier(s) in combination with oral, sublingual, buccal, nasal, pulmonary, rectal and/or trans-mucosal administration of a compound comprising N-Acetyl-L-cysteine, optionally encompassing salts, prodrugs and metabolites thereof, and optionally together with pharmaceutically acceptable carrier(s).

8. The method of claim 1, wherein the N-Acetyl-L-cysteine is administered in such a way that a therapeutically effective systemic level of N-Acetyl-L-cysteine prevails mainly during those periods of time during day and night when a mucolytic effect is most desirable.

9. The method of claim 1, wherein the N-Acetyl-L-cysteine is administered in such a way that a less than therapeutically effective systemic level of N-Acetyl-L-cysteine prevails mainly during those periods of time during day and night when a mucolytic effect is less desirable.

10. The method of claim 6, wherein the predefined period of time is 8, 12 or 24 hours.

* * * * *